(12) United States Patent
Srinivasan et al.

(10) Patent No.: US 6,425,284 B1
(45) Date of Patent: Jul. 30, 2002

(54) METHOD AND APPARATUS FOR GAS-ASSISTED SUPPRESSED CHROMATOGRAPHY

(75) Inventors: Kannan Srinivasan, Sunnyvale; Christopher A. Pohl, Union City, both of CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

(21) Appl. No.: 09/521,626

(22) Filed: Mar. 8, 2000

(51) Int. Cl.[7] .............................................. G01N 30/02
(52) U.S. Cl. .................... 73/61.52; 73/61.55; 73/61.58; 210/656; 210/198.2; 210/660; 210/668; 422/70; 436/161
(58) Field of Search ............................ 73/61.52, 61.58, 73/61.61, 61.55, 61.56, 61.57; 210/656, 660, 662, 668, 198.2; 422/70; 436/161

(56) References Cited

U.S. PATENT DOCUMENTS

| | | | |
|---|---|---|---|
| 4,265,634 A | 5/1981 | Pohl | |
| 4,834,877 A | 5/1989 | Peters et al. | |
| 4,999,098 A | 3/1991 | Pohl et al. | |
| 5,248,426 A | 9/1993 | Stillian et al. | |
| 5,352,360 A | 10/1994 | Stillian et al. | |
| 5,597,734 A | 1/1997 | Small et al. | 73/61.58 |
| 5,633,171 A | 5/1997 | Small et al. | |
| 5,773,615 A | 6/1998 | Small et al. | |
| 6,027,643 A | 2/2000 | Small et al. | |

FOREIGN PATENT DOCUMENTS

| | | |
|---|---|---|
| WO | 99/11351 | 3/1999 |
| WO | 99/44054 | 9/1999 |

OTHER PUBLICATIONS

Rabin, et al., "New Membrane–based electrolytic suppressor device for suppressed conductivity detection in ion Chromatography," *J. Chromatography*, 640:97–109 (1993).

*Primary Examiner*—Daniel S. Larkin
(74) *Attorney, Agent, or Firm*—David J. Brezner; Dorsey & Whitney LLP (57) ABSTRACT

Ionic species in an aqueous sample stream are analyzed by (a) chromatographically separating the ionic species in the presence of an aqueous eluent solution comprising electrolyte to form a chromatographic effluent, (b) suppressing the electrolyte in the chromatography effluent by flowing the same through a suppressor (e.g., a membrane suppressor) to form a suppressed effluent, (c) detecting the ionic species in the suppressed effluent, and (d) regenerating the suppressor by flowing a mixture of a gas stream and a regenerant liquid stream through the suppressor. The gas stream may be generated by flowing the detected suppressed effluent through an electrolytic gas generator which electrolyzes water in the effluent to hydrogen and oxygen gas. Also, pressurized gas may be directed into a reservoir of regenerant liquid for flow from said reservoir to said regenerant flow channel.

22 Claims, 7 Drawing Sheets

METHOD AND APPARATUS FOR GAS-ASSISTED SUPPRESSED CHROMATOGRAPHY

BACKGROUND OF THE INVENTION

The present invention relates to method and apparatus using suppression of eluents for the analysis of anions or cations in ion chromatography.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed, but not that of the separated ions so that the latter may be determined by a conductivity cell. This technique is described in detail in U.S. Pat. Nos. 3,897,213, 3,920,397, 3,925,019, and 3,926,559.

Suppression or stripping of the electrolyte is described in the above prior art references by an ion exchange resin bed commonly referred to as a packed bed suppressor (PBS). The PBS requires periodic regeneration by flushing with an acid or base solution.

Another approach to regeneration of a PBS is disclosed in U.S. Pat, No. 5,773,615. Ion chromatography is performed by chromatographic separation, chemical suppression in a packed bed, and detection. Thereafter, an electrical potential is passed through the packed bed suppressor while flowing an aqueous stream through it to electrolyze water in the stream and thereby create hydronium or hydroxide ions to regenerate the ion exchange resin. The packed bed suppressor has electrodes embedded in the resin for electrochemical regenerant. A second ion exchange resin bed is disclosed with suitable valving to pass liquid streams through the system. In one alternative, a second sample in an eluent stream is chromatographically separated. The eluent and separated second sample flow through a second packed bed suppressor and to a detector. The effluent then flows through the first packed bed suppressor, forming the aqueous liquid stream required for regeneration and an electrical potential is applied for regeneration. The second suppressor may be similarly regenerated by flowing the detector effluent of the first sample through it and applying an electrical potential.

Another form of suppressor known as a "membrane suppressor" is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant and chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the use of water to replace the regenerant solution in the electrodialytic mode.

Another membrane suppressor is described in U.S. Pat. No. 5,248,426. A direct current power controller generates an electric field across two platinum electrodes to electrolyze water in the regenerant channels. Functionalized ion-exchange screens are present in the regenerant chambers to facilitate electric current passage with permselective ion-exchange membrane defining the chromatography eluent chamber, as in the '098 patent. After detection, the chromatography effluent is recycled through the suppressor to form a flowing sump for electrolyte ion as well as providing the water for the electrolysis generating acid or base for suppression.

A different membrane suppressor is disclosed in EPA Publication WO 99/44054. The suppressor is of the membrane suppressor type even though it includes a flow-through suppressor bed of ion exchange resin. The bed has a liquid sample inlet and an outlet section, a first electrode in an electrode chamber is adjacent to the suppressor inlet section. A barrier separates the suppressor bed from the electrode chamber, preventing significant liquid flow but permitting transport of ions. A second electrode is in electrical communication with said resin bed outlet section. A recycle conduit provides fluid communication between the suppressor outlet and the electrode inlet. In one embodiment of the disclosed method for anion analysis, effluent from a chromatography column is suppressed in cation exchange resin in the suppressor. The effluent from the suppressor flows past a detector and is recycled to the electrode chamber including a cathode. An electrical potential is applied between the cathode and an anode in electrical communication with the suppressor bed. Water is electrolyzed at the anode to generate hydronium ions to cause cations on the cation exchange resin to electromigrate toward the barrier and to be transported across said barrier toward the cathode while water in the cathode chamber is electrolyzed to generate hydroxide ions which combine with the transported cations to form cation hydroxide in the electrode chamber.

SUMMARY OF THE INVENTION

According to the present invention, ionic species in an aqueous sample stream are analyzed by the method of (a) chromatographically separating the ionic species in the presence of an aqueous eluent solution comprising electrolyte to form a chromatographic effluent, (b) suppressing the electrolyte in the chromatography effluent by flowing the same through a suppressor (e.g., a membrane suppressor) to form a suppressed effluent, (c) detecting the ionic species in said suppressed effluent, and (d) regenerating the suppressor by flowing a mixture of a gas stream and a regenerant liquid stream through the suppressor.

The gas stream may be generated by flowing the detected suppressed effluent through an electrolytic gas generator which electrolyzes water in the effluent to hydrogen and oxygen gas.

Also, pressurized gas may be directed into a reservoir of regenerant liquid for flow from said reservoir to said regenerant flow channel.

The apparatus for ion analysis according to the invention includes (a) a chromatographic separator for separating ionic species in a liquid sample, (b) a suppressor for suppressing electrolyte in chromatography effluent eluting from said chromatographic separator having an inlet and an outlet, (c) a source of a regenerant liquid stream in fluid communication with the inlet of the suppressor, (d) a source of a gas stream in fluid communication with the inlet of the suppressor, and (e) a detector for detecting ionic species in the effluent from said suppressor outlet and in fluid communication therewith.

DETAILED DESCRIPTION OF THE PREFERRED EMBODIMENTS

The system of the present invention is useful for determining a large number of ionic species so long as the species to be determined are solely anions or solely cations. A suitable sample includes surface waters, and other liquids, such as industrial chemical wastes, body fluids, beverages, such as fruits and wines, and drinking water. When the term "ionic species" is used herein, it includes species in ionic form and components of molecules which are ionizable under the conditions of the present system.

In general terms, the present invention relates to the use of a gas in combination with a regenerant liquid used to regenerate the suppressor used in ion chromatography. The purpose of the suppressor is to reduce the conductivity, and hence noise, of the analysis stream background while enhancing the conductivity of the analytes (i.e., increasing the signal/noise ratio), while maintaining chromatographic efficiency. Thus, the following parameters are important to the performance of the suppressor: (1) capacity of the suppressor, measured as $\mu$Eg/mL of the suppressor resin; (2) the volume of the suppressor; (3) the ratio of the i.d. to the length of the suppressor; and (4) background conductivity measured as $\mu$S/cm for each device.

As will be described in more detail, the use of a gas stream mixed with the liquid regenerant stream provides a number of significant potential benefits. It can increase the fluid velocity through the suppressor, increase the capacity of the suppressor, increase the speed of suppression, reduce equilibration time, reduce detection noise, reduce operational and disposal costs, and reduce regenerant consumption for the non-recycle mode suppression.

The gas-assisted suppression of the present invention is applicable to any of the suppression techniques known in the art. For example, it is applicable to suppression using a membrane suppressor or packed bed as suppressor as described in the Background. Also, it is applicable to the use of an independent regenerant liquid stream or to a recycling regenerant liquid stream. It is also applicable to a suppressor which is chemically or electrolytically regenerated. Moreover, the gas may be supplied from a conventional gas source, such as a pressurized cylinder or electrochemical generated as described herein.

As used herein, the term "membrane suppressor" includes a suppressor of the general type described in U.S. Pat. Nos. 4,999,098, 5,352,360, and Publication WO99/44054 incorporated herein by reference. A membrane suppressor includes a chromatography effluent flow channel separated by a liquid impermeable ion exchange membrane from a regenerant flow channel. Effluent from the chromatography separator flows through the chromatography effluent flow channel and from there to the detector. A regenerant liquid flows in the regenerant liquid flow channel on the opposite side of the membrane. The membrane partitioning the flow channels is permselective, i.e., preferentially permeable to ions of one charge only, positive or negative, of the opposite charge to the analyte ions of interest and includes exchangeable ions of that one charge. For example, for anion analysis, the electrolyte in the eluent typically includes a strong cation such as sodium and the membrane is permeable to the sodium ions. During suppression, the sodium ions move across the membrane from the chromatography effluent flow channel to the regenerant flow channel, while hydronium ions move across the membrane from the regenerant flow channel to the chromatography effluent flow channel, thereby suppressing the chromatography effluent prior to detection.

The regenerant liquid can be a chemical regenerant, such as an acid or a base, for chemical (non-electrolytic) regeneration or can constitute water or effluent from the detector, e.g., comprising substantially water, for use as the water source for electrolytic regeneration.

As used herein, the term "ion exchange packing suppressor" refers to a suppressor in which substantially all of the suppression occurs in ion exchange material in the suppressor and regeneration occurs in a separate operation rather than simultaneously as with the membrane suppressor. The conventional form of ion exchange packing suppressor is a packed bed suppressor (PBR), such as described in U.S. Pat. No. 5,773,615. Alternatively, other forms of ion exchange packing may be employed such as a porous ion exchange monolith through which the chromatography effluent passes, such as disclosed in EPA Publication No. WO 99/11351.

Figure 1:
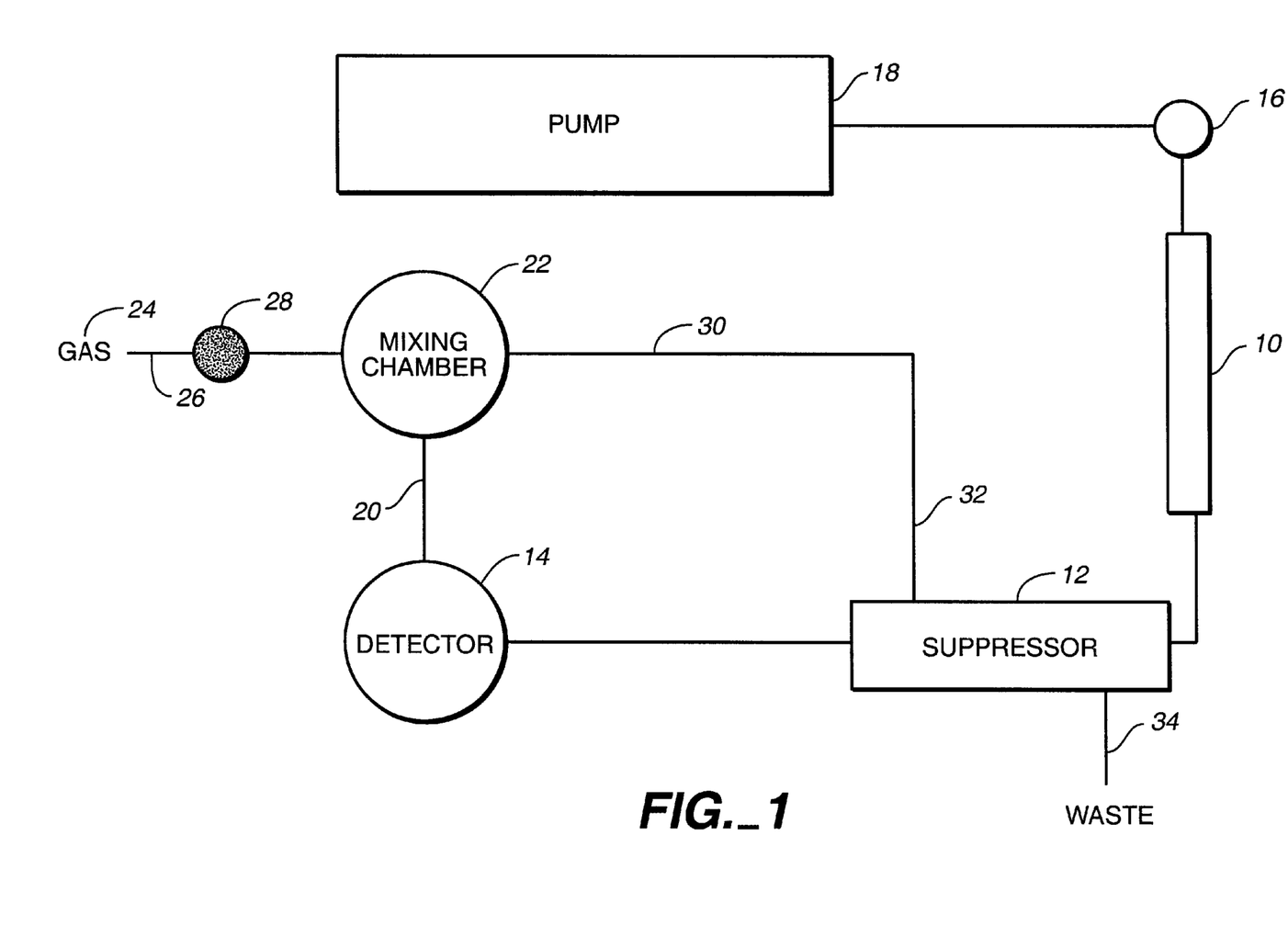
FIGS. 1–3 are different embodiments of flow systems using the gas-assisted invention.

Referring to FIG. 1, a simplified schematic drawing of one form of the present invention using gas-assisted suppression is illustrated using an external gas source and a conventional membrane suppressor. The system includes a chromatographic separator, typically in the form of a chromatography column 10 which is packed with a chromatographic separation medium. In one embodiment, such medium is in the form of ion exchange resin. In another embodiment, the separation medium is a porous hydrophobic chromatographic resin with essentially no permanently attached ion exchange sites. This other system is used for mobile phase ion chromatography (MPIC) as described in U.S. Pat. No. 4,265,634. An ion exchange site-forming compound, including a hydrophobic portion and an ion exchange site, is passed through the column and is reversibly adsorbed to the resin to create ion exchange sites.

Arranged in series with column 10 is suppressor 12 serving to suppress the conductivity of the electrolyte of the eluent from column 10, but not the conductivity of the separated ions. The effluent from the suppressor is directed to a detector 14, for detecting the resolved ionic species. A suitable sample is supplied through sample injection valve 16 which is passed through the system in the solution of eluent from an eluent source or reservoir, not shown. After pumping by pump 18, it is passed through sample injection valve 16. Detector 14 is preferably a conductivity cell in which the presence of ionic species produces an electrical signal proportional to the amount of ionic material. Such signal is typically directed to a conductivity meter, not shown, thus permitting detection of the concentration of separated ionic species. As is well known, other types of detectors may also be employed.

The effluent from detector 14 is mixed with a gas and recycled to a flow-through regenerant flow channel of the membrane suppressor 12. In a sandwich suppressor type of electrolytic membrane suppressor described in U.S. Pat. No. 5,352,360, there are two regenerant flow channels on opposite sides of a central chromatographic effluent flow channel with two ion exchange membranes partitioning the three channels. The regenerant flow channels are referred to in that patent as detector effluent flow channels. The detector effluent flows through a splitter valve which separates it into two different conduits to supply the two different regenerant flow channels. The details of this set-up and of a typical electrolytic membrane suppressor are set forth in the same patent, incorporated at this point by reference. A setup for a chemically regenerated membrane suppressor is disclosed in U.S. Pat. No. 4,999,098.

In the embodiment of FIG. 1, gas is supplied by a conventional pressurized gas source, such as a pressurized gas cylinder, and flows in a recycle conduit from detector 14 to membrane suppressor 12. Any gas may be used which does not interfere with the suppression reaction. Thus, for a membrane suppressor, it preferably excludes contaminants which can be transported across the membrane from the regenerant stream to the chromatography effluent flow channel at a sufficient concentration to significantly interfere with detection. A suitable gas source is relatively inert including helium, nitrogen, and argon. If air is of sufficient purity, compressed air may also be used as a gas source. As set out below, electrolytically generated hydrogen and oxygen gases may also be used.

Referring again to FIG. 1, liquid effluent from detector 14 flows through a conduit 20 to a mixing chamber illustrated in the form of mixing T-connector 22. A gas source, typically a compressed gas cylinder 24, flows through line 26 to mixing T 22. A check valve 28 may be included in line 26 serving the function of minimizing liquid transport back into the gas lines in the event no gas is flowing or the gas supply is exhausted. The gas and liquid mixture formed in mixing T 22 flows through line 30 to the inlet 32 of suppressor 12, specifically the inlet of the regenerant flow channel. As set out above, the regenerant liquid flows on one side of the ionic exchange membrane while the chromatography effluent flows on the other side. The electrical conductivity of the electrolyte in the eluent is suppressed. The regenerant liquid exits the suppressor in line 34 and flows to waste.

In the form of membrane suppressor illustrated in U.S. Pat. No. 5,352,360, suppression occurs electrochemically. As disclosed there, it is preferable to include a form of flow-through ion exchange or conductive materials such as a charged screen, in the chromatography effluent flow channel and regenerant flow channel to assist the transport of the electrolyte ions across the membranes for suppression. An electrical potential is applied between spaced electrodes communicating on the one hand with the regenerant flow channel and the other hand with the chromatography effluent flow channel. The chemical reactions are illustrated in FIG. 4 of that patent for a typical anion analysis system. As is illustrated, the sodium hydroxide is the electrolyte of the eluent which is converted into weakly ionized form ($H_2O$) in the suppressor. Thereafter, the solution, passes through the conductivity cell and is recycled to the detector effluent flow channel. The ion exchange membrane sheets allow the positively charged sodium and hydronium ions to permeate across the membrane. The method and device using an electrochemical membrane suppressor are described in detail in U.S. Pat. No. 5,352,360, and in using a chemically regenerated suppressor are described in U.S. Pat. No. 4,999,098, both incorporated at this point by reference.

In the embodiment of FIG. 1, sufficient gas is mixed with the flowing regenerant liquid to accomplish at least some of the aforementioned advantages. Typical flow rates for the detector effluent are on the order of about 0.1 to 10 ml/min, and preferably about 0.2 to 3 ml/min, and more preferably about 0.25 to 2 ml/min. Correspondingly, typical flow rates for the gas stream mixed with the detector effluent are about 2 to 500 ml/min, and more preferably about 20 to 150 ml/min. A suitable ratio of gas:regenerant liquid flow rate is about 1:1 to about 5000:1, preferably about 10:1 to 1500:1, more preferably about 30:1 to 150:1.

In this type of system, the gas introduced into the liquid suitably is supplied from a pressurized gas source maintained at a pressure of at least about 1 psi, preferably at least about 5 psi, and most preferably at least about 10 psi. The pressure should not be so high as to cause damage to the suppressor device. Thus, it is preferable that the upper end of the pressure range is suitably not greater than about 100 psi, more preferably no greater than about 30 psi, and most preferably no greater than about 15 psi. It should be noted that beyond an optimal gas pressure or gas flow rate there is little benefit in increasing the pressure or flow rate any further. The increased velocity of the gas aids efficient removal of both electrolytic gases and liquid from the regenerant chamber, thus homogenizing the flow in the regenerant chamber. Beyond an optimal gas flow, there may be no benefit in increasing the gas flow rate, and any further increase in the gas velocity may actually result in higher gas wastes with no added benefit in terms of noise or performance.

A ratio of peak-to-peak noise in the gas-assisted mode versus the no-gas approach when operated using a membrane suppressor under the recycle mode typically is in the range of 1:2 to 1:20, more typically a ratio of 1:4 to 1:10.

Figure 2:
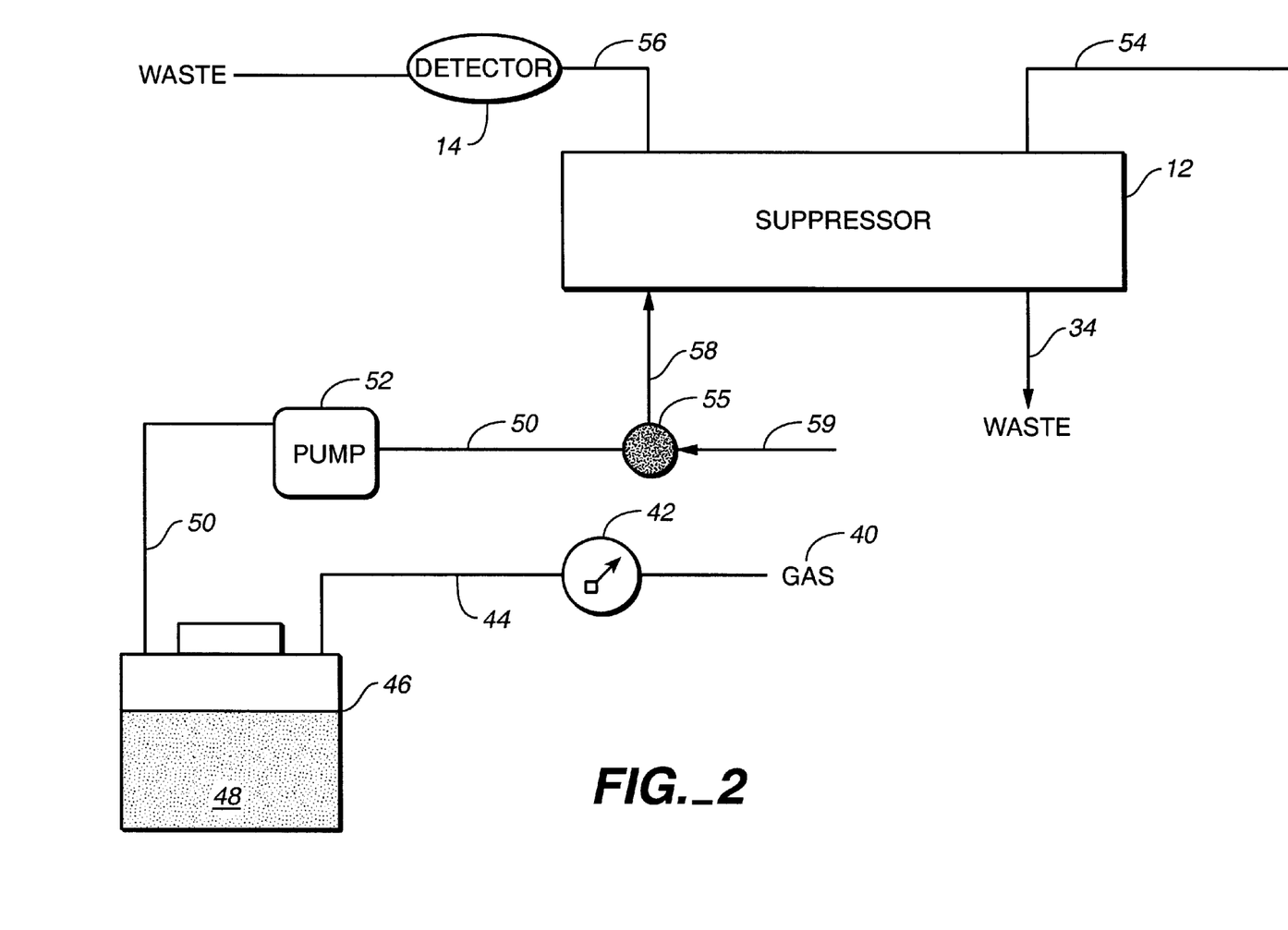

Referring to FIG. 2, another embodiment of the invention is illustrated in which the regenerant liquid is supplied to the membrane suppressor from an external source in the form of a regenerant liquid reservoir in a container and wherein the gas is supplied to the regenerant liquid reservoir. This flow system of FIG. 2 includes many of the same components as the flow system of FIG. 1, but there is no regenerant liquid recycle. Like parts will be designated with like numbers for FIGS. 1 and 2. In this instance, gas is suitably supplied from the pressurized cylinder or other gas supply 40 controlled by regulator 42 and is directed in line 44 into container 46 containing a reservoir of regenerant liquid 48. Suitably, container 46 is a conventional laboratory plastic cylindrical bottle of the desired size. The regenerant liquid may be a chemical regenerant, such as an acid or base, used for chemical regeneration of the membrane suppressor, as illustrated, for example, in U.S. Pat. No. 4,999,098. Here, the gas may be pressurized under sufficient pressure so that the gas supplies the means for pressurizing the liquid to pump it through the regenerant flow channel of suppressor 12. Gas is also supplied from a suitable source 59, such as a pressurized gas cylinder, between container 46 and suppressor 12. The gas from source 59 is mixed with regenerant liquid in line 50 in a suitable mixing chamber, such as mixing T 55, for supply in line 58 to the regenerant flow channel inlet of suppressor 12.

The regenerant liquid flows out of reservoir 48 into line 50 and is pumped into the inlet of the regenerant flow channel of membrane suppressor 12. If the gas pressure is not used to drive all of the liquid regenerant flow through the membrane suppressor, then a pump 52 of a conventional type may be used for this purpose. The chromatography effluent from the chromatographic separator (not shown) flows in line 54 into membrane suppressor 12 and out line 56 through detector 14 and to waste. If membrane suppressor 12 is an electrolytic suppressor, as described in U.S. Pat. No. 5,352,360, then the liquid in reservoir 48 preferably is pure water, or may be acid for anion analysis or base for cation analysis. On the other hand, if membrane suppressor 12 is not electrolytic, then the regenerant liquid preferably is an acid or base as described in U.S. Pat. No. 4,999,098.

The container for the regenerant liquid reservoir is sized to contain a sufficient volume of regenerant liquid for the desired regeneration. For some systems, depending on the size of the chromatographic column and suppressor, a volume of at least about 500 ml is sufficient. For other systems, the volume may be at least about 1000 ml to as large as about 4000 ml or more. Multiple containers in series or parallel may also be employed. The term "container" herein refers to one or more containers.

Figure 3:
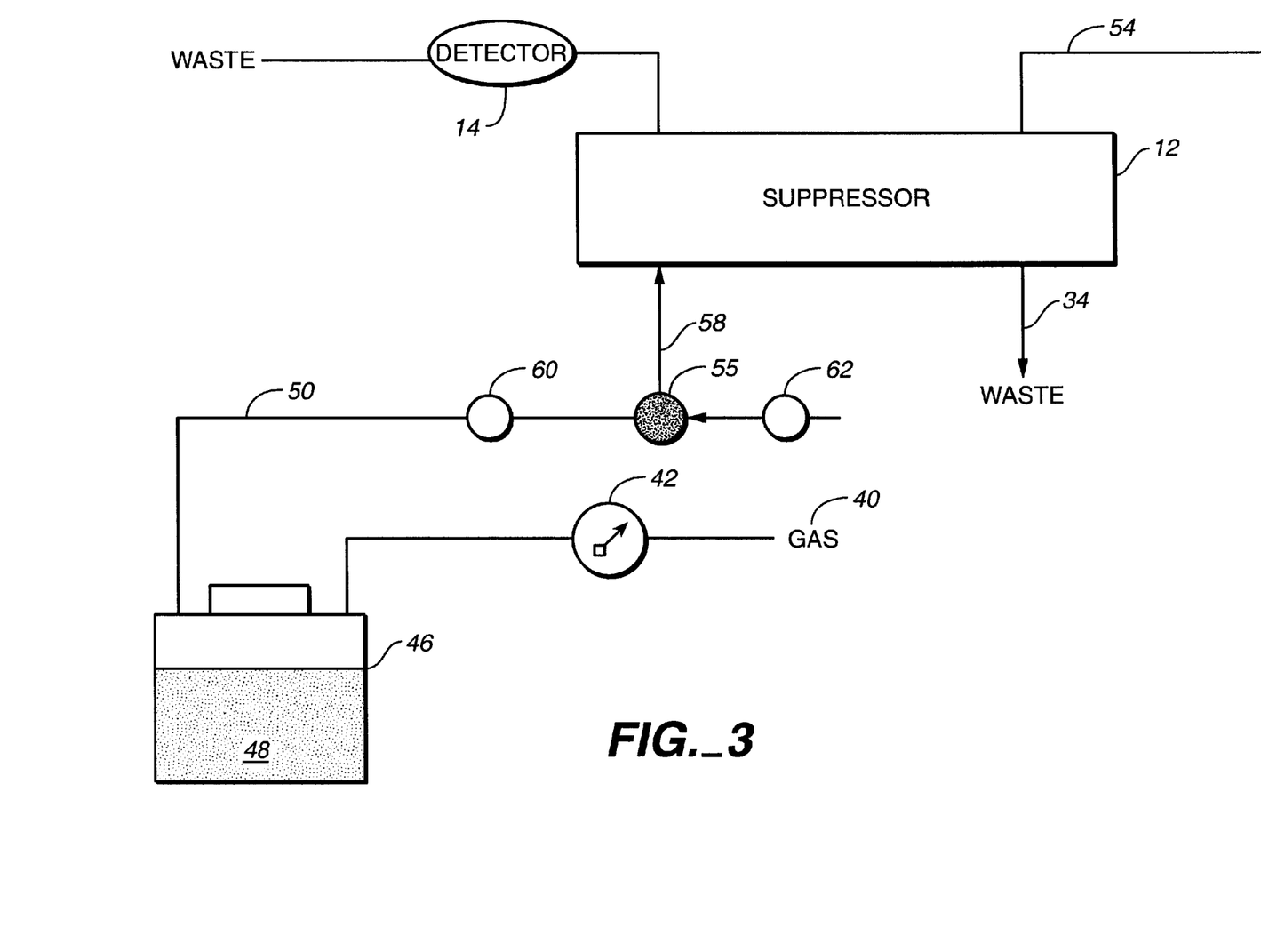

Referring to FIG. 3, another embodiment of the system of FIG. 2 is illustrated with the exception that pump 52 is eliminated. Here, a liquid check valve 60 is included in line 50 serving the purpose of ensuring liquid flow in one direction and no gas flow in the opposite direction. Similarly, a gas check valve 62 is included in the gas supplied to mixing T 55 and serving the purpose of ensuring gas flow in the required direction and no liquid flow in the opposite direction.

Figure 4:
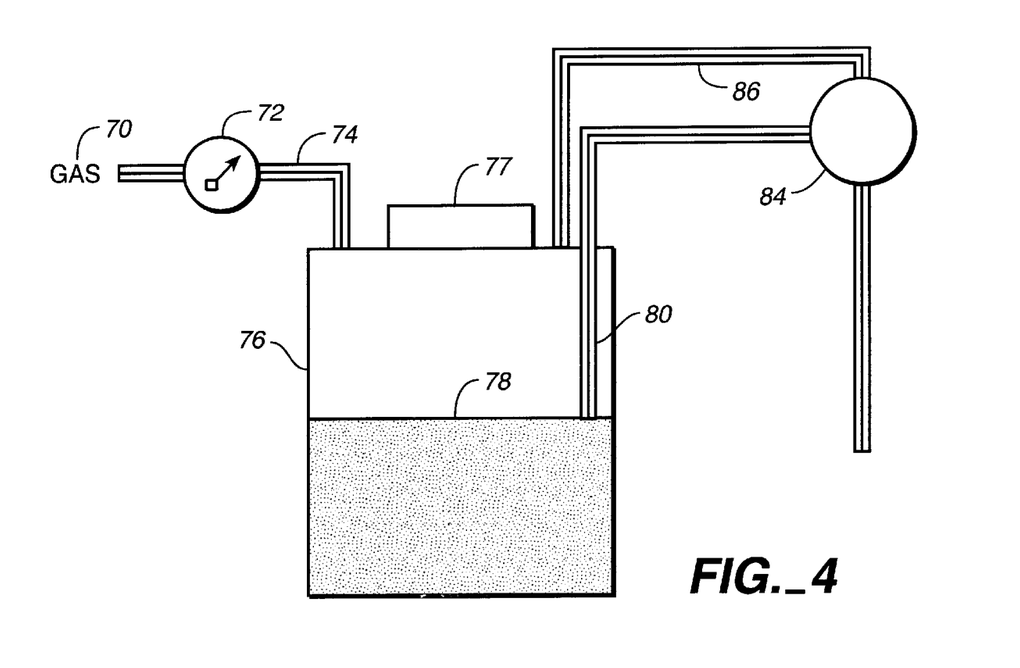
FIGS. 4, 5, and 5A are embodiments of gas-assisted reservoirs according to the invention.

FIG. 4 illustrates one embodiment of a system for pumping gas into a reservoir of regenerant liquid to supply a mixture of the gas and liquid to the regenerant suppressor. This system can be operated with or without an additional pump. Gas from a pressurized supply 70 controlled by regulator 72 flows through line 74 into container 76 suitably in the form of a bottle with an inlet opening closed by stopper 77. The regenerant liquid reservoir is illustrated by the number 78. The gas enters container 76 near the top of the container. A liquid conduit suitably projects through the top of container 76 and extends to a sufficient level or depth within the container to be below the selected level of the liquid reservoir 78 at completion of the regenerant run. The regenerant liquid suitably is supplied to the container top opening with stopper 77 removed. After filling stopper 77 is inserted and pressurized, gas flows into container 76 from source 70. The liquid exiting container 76 flows through tubing 80 to a suitable mixing chamber in the form of mixing T 84. Another conduit in the form of gas tubing 86 communicates with the interior of container 76 at its inlet end and with mixing T 84 at its outlet end. The gas-liquid mixture formed in mixing T 84 is then directed to the regenerant inlet of a membrane suppressor or an ion exchange packing suppressor. The additional pressure used for this purpose, if any, is added to the numerical pressure values set out above.

Figure 5:
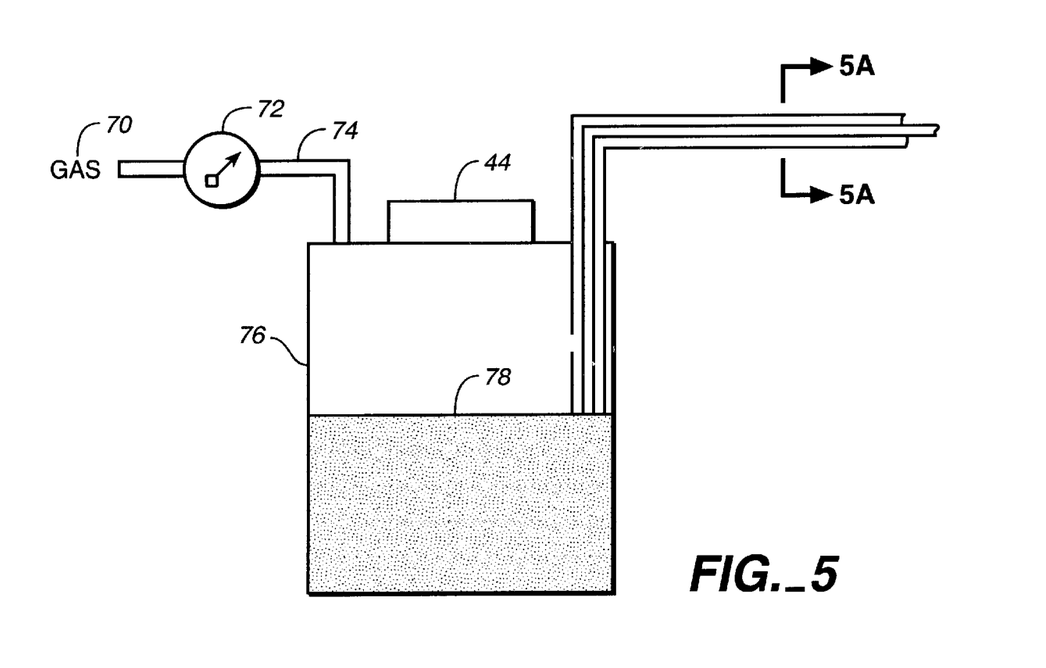
Figure 5A:
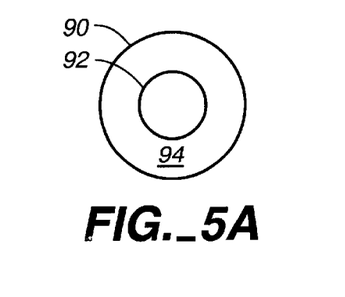

Referring to FIG. 5, another form of gas mixing and pressurizing device is illustrated which is similar to the embodiment of FIG. 4. Accordingly, like parts will be designated with like numbers. The principal difference between the illustrated systems is the way in which the regenerant liquid and gas are mixed. Here, concentric tubes 90 and 92 are employed as illustrated in FIG. 5A. Tubes 90 and 92 project below the selected level of regenerant liquid 78 at the end of a suppression cycle. The gas flowing into container 76 through line 74 pressurizes the liquid in reservoir 78 and causes it to flow in liquid tubing 92 out of container 76. A portion of the gas flows through an opening in tube 90 and into the flow channel 94 created in the annular space between tubes 90 and 92. The distal end of tube 90 is suitably connected to the inlet of the suppressor to supply the regenerant liquid. Liquid tube 92 terminates in an opening within tube 90 upstream of the suppressor inlet. In this way, at this termination point, the liquid and gas are mixed forming a mixing chamber of a similar function to the mixing T described above. The parameters described above for the liquid and gas also apply to this embodiment. Alternatively, the conduits for the gas and liquid can be reversed with appropriate modification of the openings.

The systems illustrated in FIGS. 1–3 use a membrane form of suppressor in which suppression occurs simultaneous with regeneration across an ion exchange membrane. However, the gas-assisted invention can be used with appropriate modifications to an ion exchange packing suppressor, e.g., a packed bed suppressor. For purposes of this discussion, the invention will be described with respect to a conventional packed bed suppressor. Here, regeneration occurs after, not simultaneously with, suppression after the selected degree of exhaustion of the packed bed during suppression. In a well-known technique for chemical regeneration, an acid or base is directed through the suppressor for regeneration. For example, to regenerate a suppressor which is exhausted by the presence of sodium ions, an acid is flowed through the suppressor to reconvert the ion exchange resin to hydronium ion form. This can be accomplished in a batch operation with a single suppressor. Alternatively, two suppressors may be employed with appropriate valving so that when one suppressor is on-line, the other suppressor is being regenerated. One system of this type is illustrated in U.S. Pat. No. 5,597,734.

In another system, the packed bed suppressor may be regenerated electrolytically. A system of this type is illustrated in U.S. Pat. No. 5,633,171, incorporated herein by reference. This system may be employed with a single suppressor or two suppressors with appropriate valving. In the latter instance, one suppressor is being regenerated while the other one is on-line and then the roles are reversed. One form of valving is to flow the detector effluent primarily comprising water and analytes to the other suppressor as the regenerant liquid. In this instance, the regenerant liquid supplied to the packed bed suppressor is analogous to the regenerant liquid recycle stream in FIG. 1. Thus, the gas can be added to this detector effluent in the line between the detector and the packed bed suppressor being regenerated while the other suppressor is on-line. The same source of gas may be used for this packed bed suppressor as for the membrane suppressor as described above.

Gas generators may be employed instead of pressurized gas containers. For example, the hydrogen and oxygen gases generated during electrochemical suppression as in the membrane suppressor of U.S. Pat. No. 5,248,426 or in the packed bed suppressor of U.S. Pat. No. 5,633,171 can be used. They are generated and entrained in a liquid which can be used as the regenerant liquid-gas mixture. Other sources of gases such as commercially available on-line gas generators, for example a hydrogen gas generator from Matheson Tri-gas, could also be used.

Figure 6:
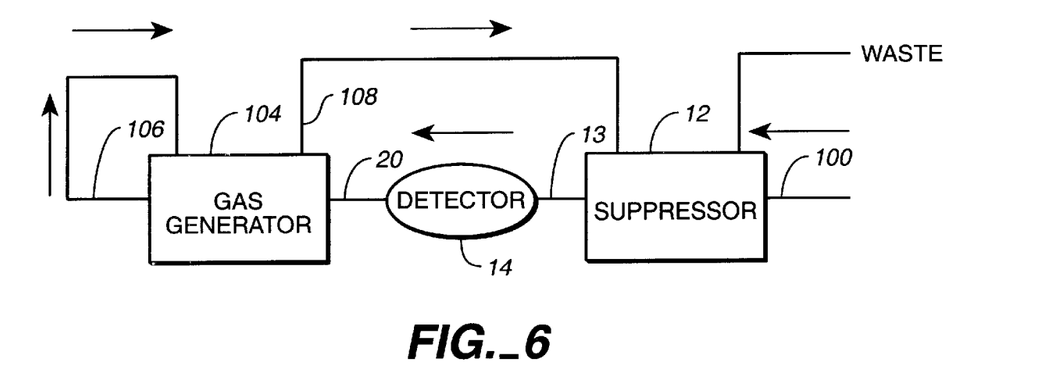
FIGS. 6 and 7 are embodiments of flow systems using gas generators according to the invention.

Referring to FIG. 6, a schematic representation of a gas generator in the form of a second membrane suppressor is illustrated. Like parts will be designated with like numbers for the membrane suppressor as set out in above FIG. 3. The liquid from chromatographic separator 10 flows through line 100 through the chromatography effluent flow channel of suppressor 12. The suppressor effluent flows in line 13 to detector 14 out line 20 and then to a gas generator 104 into the form of a second electrolytic membrane suppressor device of the type disclosed in U.S. Pat. No. 5,352,360 but not serving the function of suppression.

For a sandwich-type generator 104, the detector effluent in line 20 flows through the central channel of generator 104 corresponding to the chromatographic separation flow channel of suppressor 12. The outlet from this channel flows through line 106 and is recycled to the outside or sandwiching flow channels of generator 104 using a suitable splitter valve of the type described above. The liquid in the outside channels including the electrolytically generated hydrogen and oxygen gas exits through line 108 and is split for flow through the regenerant flow channel of suppressor 12. The generation of the hydrogen and oxygen gases is illustrated in U.S. Pat. No. 5,352,360. The electrolytic conditions and flow rates in generator 104 are selected to provide for a sufficient quantity of hydrogen and oxygen gas generation so that the gases are present at a pressure and flow rate in the effluent described above. There is a direct relationship between the applied current and the gas flow generated electrolytically. For example, for a current of 1 A applied across the electrodes, this current will generate roughly 14 ml/min of gas (hydrogen and oxygen) at STP. The volume of the pressurized gas depends on the backpressure of the suppressor device. Assuming a backpressure of 5 psi, based on Boyle's law the device would generate gas at the rate of roughly 40 ml/min at an applied current of 1 A.

Figure 7:
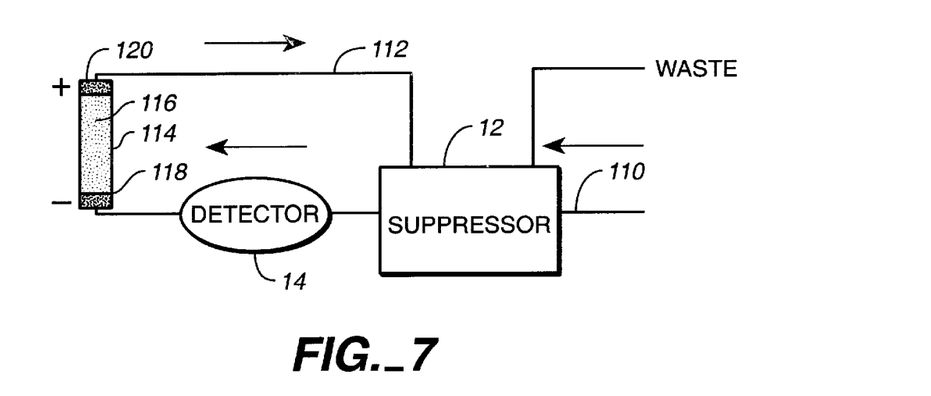
Figure 8:
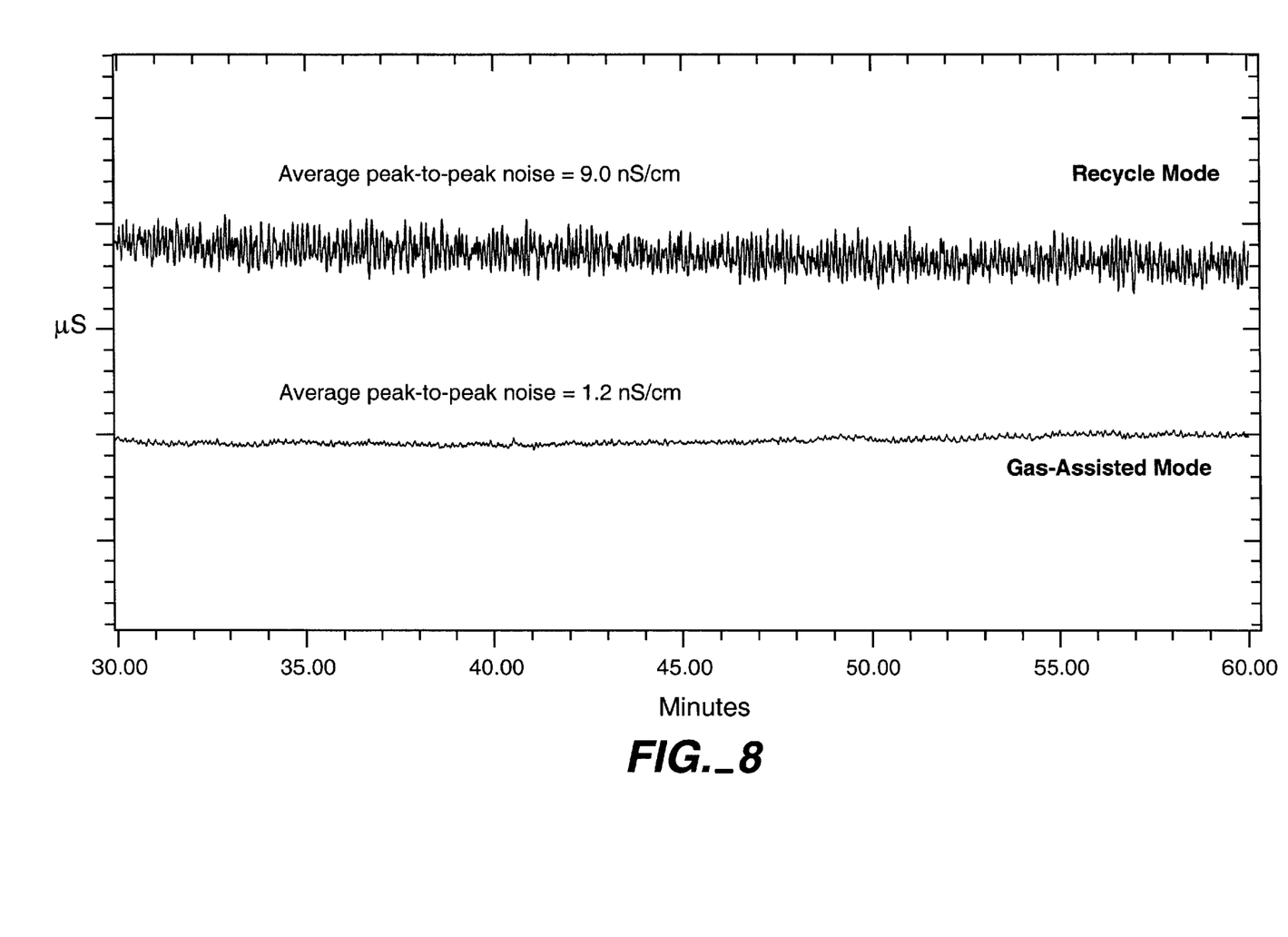
FIGS. 8 and 9 are experimental results illustrating reduction in detection noise according to the invention.

Referring to FIG. 7, another form of electrolytic gas generator is illustrated using an electrolytic ion exchange resin device of the type described in U.S. Pat. No. 5,633,171 or other electrolytic ion exchange packing suppressor. In this instance, eluent from column 10 enters line 100 into suppressor 12 and flows to detector 14 and is recycled in line 112 to the suppressor. The generator includes a flow-through housing 114, typically including a packed resin bed 116, and spaced electrodes 118 and 120, suitably at opposite ends of the packing in the housing as illustrated in FIG. 8. The packing in the column can be of an anion exchange type, cation exchange type, or any mixture thereof. The principles of electrolysis in such devices is set forth in U.S. Pat. No. 5,633,171. During electrolysis, hydrogen and oxygen gases are created as a by-product. In this instance, hydrogen and oxygen gases are carried in a stream flowing through line 112 for recycle to the membrane suppressor 12. Thus, the electrochemical principles of regeneration are used to provide the source of gas for gas-assisted regeneration. Any modification of the parameters of electrochemical regeneration set forth in U.S. Pat. No. 5,633,171 will be recognized by those of skill in the art.

Although the generators above are illustrated with respect to a recycle stream, they could also be employed for use with an external reservoir of regenerant liquid as illustrated in FIGS. 2–5.

Commercially available membrane suppressor devices of the prior art recommend a flow rate of regenerant in the 5–10 ml/min range when the eluent flow rate is in the 1–2 ml/mn range. Such high flow rates, however, can result in excessive regenerant consumption and associated waste. Additionally, the above approach necessitates the use of large reservoirs and adds to the operational and disposal costs. In the electrolytic mode when lower system noise and higher suppression capacity are required, higher flow rate of the regenerant or water (up to 10 ml/min) is recommended [Rabin, et al., *J. Chromatography*, 640:97–109 (1993)]. Typically, this is achieved by using a pressurized reservoir or by using a pump, thus increasing the regenerant consumption, which leads to increased wastes and associated operational and disposal costs.

The gas-assisted mode of operation reduces the regenerant requirement as illustrated in the preferred embodiments and examples. Reduced regenerant consumption and reduced wastes lower the operational costs of an ion chromatograph.

One way to quantify the reduction in liquid consumption is by reference to the low liquid regenerant flow rates that can be used without producing excessive noise. Without gas, typical flow rates of regenerant liquid into a membrane suppressor for low noise levels are about 10 ml/min in comparison to a typical eluent flow rate of about 1 ml/min. Thus, to minimize noise in a recycle mode, an additional 9 ml/min of regenerant liquid from an external regenerant liquid source may be added to the detector effluent being supplied to the suppressor. In contrast, the use of gas can lower the flow of regenerant liquid to that recycled from the detector (e.g., to as low as 1 ml/min), thereby eliminating the external source of regenerant liquid in the recycle mode. For any of the foregoing embodiments of the invention, the gas-assisted mode can significantly reduce the amount of regenerant liquid used to achieve low noise levels to less than about 8–10 ml/min to as low as about 3 to 5 ml/min or less, or even to 1–2 ml/min, or less than 1 ml/min.

Devices of any of the foregoing type have the common feature of directing a gas through the suppressor along with the regenerant liquid. As set forth above, this use of a gas addition to the regenerant liquid can provide one or more of the following advantages: (1) reduced regenerant consumption for ion chromatography applications; (2) reduced waste; (3) reduced operational and disposal cost; (4) reduced peak-to-peak noise and drift during detection; and (5) stabilizing of the voltage across the suppressor.

If desired, the detector effluent can be recycled to a container of regenerant liquid for use in suppression as described in application entitled DISPLACEMENT CHEMICAL REGENERATION METHOD AND APPARATUS, filed simultaneously herewith Ser. No. 09/520,731.

In order to illustrate the present invention, the following examples of its practice are provided.

EXAMPLE 1

A Dionex Corporation DX500 ion chromatography system was used for anion analysis. The analytical column was an AS11 column from Dionex Corporation, and the eluent was 21 mM NaOH at a flow rate of 1 ml/min. The suppressor was a Dionex Corporation 4-mm ASRS Ultra suppressor. The experimental setup for the gas-assisted recycle mode of operation for the suppressor is as shown in FIG. 1. The above setup resulted in complete suppression of 21 mM sodium hydroxide. The background conductivity trace for a thirty minute section of a run is shown in FIG. 8. The results indicate a reduction in noise by a factor of 7.5 in going from the recycle mode to the gas-assisted mode. The background also decreased by roughly 0.7 $\mu$S/cm suggesting minimal transport of species back from the regenerant chamber to the eluent chamber. Such low noise will improve detection limits for ion chromatographic applications.

EXAMPLE 2

A Dionex Corporation DX500 ion chromatography system was used for anion analysis. The analytical column was an AS10 column from Dionex Corporation, and the eluent was 100 mM NaOH at a flow rate of 1 ml/mmn. The suppressor was a Dionex Corporation 4-mm ASRS Ultra suppressor. Gas-assisted recycle setup was as shown in FIG. 1. The above setup resulted in complete suppression of the 100-mN sodium hydroxide eluent and excellent separation of a test mixture of five anions was achieved. The average unfiltered peak-to-peak noise for several one minute sections was within 1 nS/cm. The analytes were (1) fluoride 2 mg/L; (2) chloride 3 mg/L; (3) sulfate 15 mg/L. (4) phosphate 15 mg/L; and (5) nitrate 10 mg/L. Such low peak-to-peak noise for such a high eluent strength translates directly into lower detection limits.

EXAMPLE 3

Figure 9:
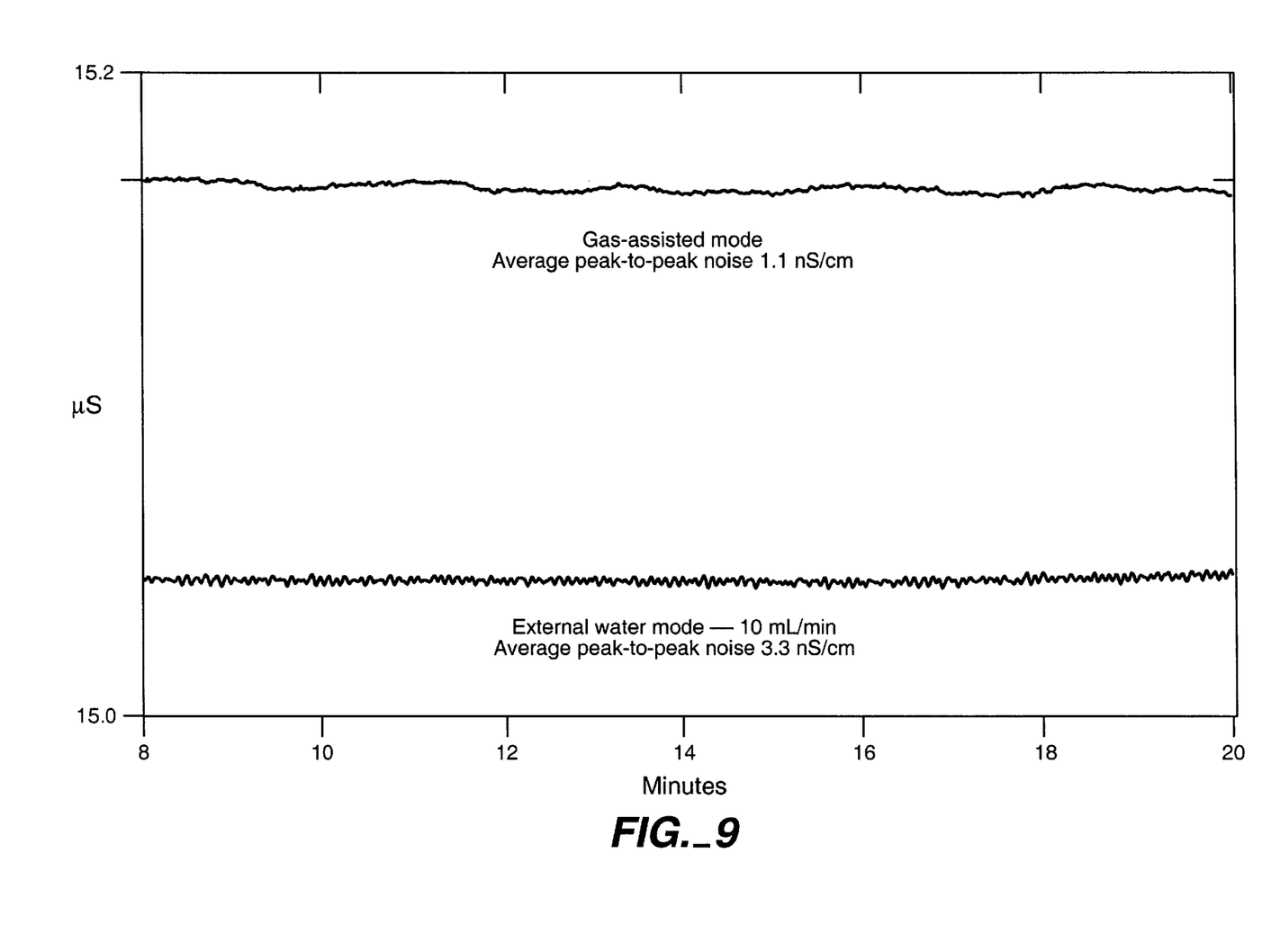

The performance of a Dionex Corporation Ultra ASRS suppressor is compared under the external water to that of the gas-assisted mode of operation. A conventional external water a setup was used with a flow rate of approximately 10 ml/min of external water. The experimental setup for the gas-assisted regeneration mode is as shown in FIG. 1. The gas-assisted regeneration was done in the recycle mode using nitrogen at an applied pressure of 10 psi. A DX500 ion chromatography system was used for anion analysis. The analytical column was AS4a from Dionex Corporation, and the eluent was 1.8 mM sodium carbonate/1.7 mM sodium bicarbonate at a flow rate of 2 ml/min. The suppressor was a 4 mm ASRS Ultra suppressor. Complete suppression occurred in both modes showing comparable separation and peak responses. The analytes were (1) fluoride 2 mg/L, (2) chloride 3 mg/L; (3) nitrate 10 mg/L; (4) phosphate 15 mg/L; and (5) sulfate 15 mg/L. The external water mode used approximately 10 ml/min of water and generated roughly 11 ml/min of waste (water combined with cell effluent). The gas-assisted mode used 1 ml/min of the cell effluent and generated only 1 ml/min of waste. Additionally, the noise was roughly three times lower for the gas-assisted mode as shown in FIG. 9. Thus, the gas-assisted regeneration provides improved performance, ease of use combined with lower operational and disposal costs.

EXAMPLE 4

The effect of the type of gas on peak-to-peak noise was studied using the gas-assisted regeneration mode. A DX500 ion chromatography system was used for anion analysis. The analytical column was AS10 from Dionex Corporation, and the eluent was 100 mM NaOH at a flow rate of 1 ml/min. The suppressor was a 4-mm ASRS Ultra suppressor. Gas-assisted recycle setup was as shown in FIG. 1. The above setup resulted in complete suppression of the 100-mN sodium hydroxide eluent. Various gases such as (1) helium; (2) nitrogen, and (3) compressed air were studied and compared to the recycle mode setup as shown in FIG. 1. In this comparison, the peak-to-peak noise for the gas-assisted regeneration mode was roughly three to four times lower than the conventional recycle mode of operation without gas.

EXAMPLE 5

This example compares the dynamic capacity of the suppressor in the conventional chemical suppression mode vs. the gas-assisted chemical suppression mode. A conventional chemical suppression setup was used with an external regenerant liquid reservoir pumped without gas. The regenerant was 50 mN sulfuric acid. A Dionex DQP pump was used for pumping the regenerant. A DX500 ion chromatography system was used for anion analysis. The analytical column was AS10 from Dionex Corporation, and the eluent was 100 mM NaOH. The suppressor was a 4-mm ASRS Ultra suppressor. Gas-assisted regeneration setup was as shown in FIG. 3 with an applied pressure of 12.5 psi. In the above setup, in order to determine the dynamic capacity, the flow rate of the analytical pump was varied while the regenerant pump was kept fixed at 6 ml/min. The dynamic capacity in the conventional regeneration mode was estimated as 90 $\mu$eqv/min. The dynamic capacity in the gas-assisted regeneration mode was 118 $\mu$eqv/min, roughly 30% higher. Thus, the addition of gas enables lowering the chemical regenerant requirement.

EXAMPLE 6

This example shows another experimental setup for implementing the gas-assisted chemical regeneration mode. The experimental setup is shown in FIG. 6 and this setup relies on a single applied pressure to drive both the regenerant and the gas. A DX500 ion chromatography system was used for anion analysis. The analytical column was AS10 from Dionex Corporation, and the eluent was 100 mM NaOH. The suppressor was a 4-mm ASRS Ultra suppressor. The regenerant was 100 mN sulfuric acid. The regenerant reservoir was pressurized to 15 psi which generated a flow of regenerant of approximately 2.88 ml/min. The dynamic suppression capacity was determined by adjusting the flow rate of the analytical pump. The dynamic capacity was approximately 115 $\mu$eqv/min. The ratio of the regenerant to the dynamic capacity was roughly 2.5. The same dynamic capacity was achieved in the conventional chemical suppression mode by pumping 100 mN sulfuric acid at approximately 7 ml/min. The ratio of the regenerant to the dynamic capacity in this case is roughly six. Thus, the gas-assisted mode reduces chemical regenerant consumption and wastes and provides operational cost benefits.

What is claimed is:

1. A method for analysis of ionic species in an aqueous sample stream comprising:

(a) chromatographically separating ionic species in said sample stream in the presence of an aqueous eluent solution comprising electrolyte to form a chromatographic effluent, (b) suppressing the electrolyte in the chromatography effluent by flowing the same through a suppressor to form a suppressed effluent, (c) detecting said ionic species in said suppressed effluent, and (d) regenerating said suppressor by flowing a mixture of a gas stream and a regenerant liquid stream through said suppressor.

2. The method of claim 1 in which said electrolyte includes transmembrane ions of opposite charge to said ionic species, said suppressor is a membrane suppressor comprising a chromatography effluent flow channel separated by a permselective ion exchange membrane, of the same charge as said transmembrane electrolyte ions, from a regenerant flow channel, and in which said gas and regenerant liquid stream mixture flows through said regenerant flow channel, and regenerating and suppressing occurs simultaneously.

3. The method of claim 2 in which said detected suppressed effluent is recycled to said regenerant flow channel and comprises a source of said regenerant liquid stream.

4. The method of claim 3 in which said gas stream is mixed with said regenerant liquid stream source after step (c) and prior to flowing through said regenerant flow channel.

5. The method of claim 1 further comprising the step of
(e) generating said gas stream by flowing said detected suppressed effluent through an electrolytic gas generator which electrolyzes water in said effluent to hydrogen gas and oxygen gas which comprise said gas stream.

6. The method of claim 1 together with the step of flowing pressurized gas into a reservoir of said regenerant liquid to cause said regenerant liquid to flow from said reservoir to said regenerant flow channel.

7. The method of claim 6 in which at least a portion of said pressurized gas comprises said gas stream which flows from said reservoir to said suppressor.

8. The method of claim 7 in which said gas stream flows from said reservoir in a first conduit, said regenerant liquid flows from said reservoir in a second conduit, and said gas stream and regenerant liquid stream in said first and second conduits, respectively, are mixed prior to flow into said suppressor.

9. The method of claim 1 in which said regenerant liquid comprises a chemical regenerant and said suppressing is performed by chemical suppression.

10. The method of claim 1 in which said suppressing is performed electrochemically.

11. The method of claim 1 in which said suppressor is a flow-through ion exchange packing suppressor and said regenerating occurs after completion of said detecting.

12. The method of claim 11 in which said suppressing is performed chemically and said regenerant liquid stream comprises an acid or base.

13. The method of claim 11 in which said regenerating is performed electrolytically by applying a voltage across said ion exchange packing while flowing said regenerant liquid stream therethrough.

14. Apparatus for ion analysis comprising:
(a) a chromatographic separator for separating ionic species in a liquid sample,
(b) a suppressor for suppressing electrolyte in chromatography effluent eluting from said chromatographic separator having an inlet and an outlet,
(c) a source of a regenerant liquid stream in fluid communication with the inlet of said suppressor,
(d) a source of a gas stream in fluid communication with the inlet of said suppressor, and
(e) a detector for detecting ionic species in the effluent from said suppressor outlet and in fluid communication therewith.

15. The apparatus of claim 14 in which said suppressor comprises a membrane suppressor including a chromatography effluent flow channel separated by an ion exchange membrane from a regenerant flow channel and said suppressor inlet comprises an inlet of said regenerant flow channel.

16. The apparatus of claim 15 further comprising a recycle conduit for directing effluent from said detector to said regenerant flow channel inlet.

17. The apparatus of claim 16 further comprising a mixing chamber for mixing said regenerant liquid stream with said gas stream and disposed along said recycle conduit between said detector and said regenerant flow channel inlet.

18. The apparatus of claim 14 in which said regenerant liquid source further comprises a reservoir for regenerant liquid having an inlet and a regenerant liquid outlet communicating with said suppressor inlet and further comprising
(f) a source of pressurized gas communicating with the said reservoir inlet for pressurizing regenerant liquid therein for flow from said reservoir regenerant liquid outlet to said suppressor inlet.

19. The apparatus of claim 18 in which said reservoir further includes a gas stream outlet in fluid communication with said suppressor inlet.

20. The apparatus of claim 19 further comprising a mixing chamber, a first conduit connecting said regenerant liquid outlet and said mixing chamber, and a second conduit connecting said gas stream outlet and said mixing chamber, said mixing chamber being in fluid communication with said suppressor inlet.

21. The apparatus of claim 14 further comprising
(f) an electrolytic gas generator adapted to electrolyze water flowing through it to generate hydrogen and oxygen gas, said generation being disposed between said detector and said suppressor inlet.

22. The apparatus of claim 14 in which said suppressor is a flow-through ion exchange packing suppressor.

* * * * *